United States Patent
Norcross, Jr.

(10) Patent No.: US 8,313,230 B2
(45) Date of Patent: Nov. 20, 2012

(54) MIXERS FOR A VISCOMETER AND METHODS FOR USING THE SAME

(75) Inventor: Robert A. Norcross, Jr., Newton, MA (US)

(73) Assignee: Norcross Corporation, Newton, MA (US)

(*) Notice: Subject to any disclaimer, the term of this patent is extended or adjusted under 35 U.S.C. 154(b) by 0 days.

(21) Appl. No.: 13/223,764

(22) Filed: Sep. 1, 2011

(65) Prior Publication Data
US 2012/0075949 A1     Mar. 29, 2012

Related U.S. Application Data

(63) Continuation of application No. PCT/US2010/028467, filed on Mar. 24, 2010.

(60) Provisional application No. 61/162,802, filed on Mar. 24, 2009.

(51) Int. Cl.
*B01F 11/00* (2006.01)

(52) U.S. Cl. ....... 366/142; 366/276; 73/54.15; 73/54.18

(58) Field of Classification Search ............ 366/142, 366/243, 276, 278; 73/54.15, 54.18
See application file for complete search history.

(56) References Cited

U.S. PATENT DOCUMENTS

| | | | |
|---|---|---|---|
| 2,491,389 A * | 12/1949 | Norcross | 73/54.18 |
| 2,630,819 A * | 3/1953 | Norcross | 137/92 |
| 3,512,396 A * | 5/1970 | Okamoto | 73/54.21 |
| 3,686,931 A | 8/1972 | Norcross | |
| 5,677,481 A | 10/1997 | Brown et al. | |
| 5,704,382 A | 1/1998 | Hoffmann et al. | |
| 5,959,196 A | 9/1999 | Norcross, Jr. | |
| 6,928,860 B1 | 8/2005 | Hildebrandt et al. | |
| 2005/0087002 A1 | 4/2005 | Kanzaki et al. | |

FOREIGN PATENT DOCUMENTS

| GB | 2423584 A | 8/2006 |
|---|---|---|
| JP | 11-295205 A | 10/1999 |

OTHER PUBLICATIONS

International Search Report for International Application No. PCT/US2010/028467 (Jul. 16, 2010).
Written Opinion for International Application No. PCT/US2010/028467 (Jul. 16, 2010).

* cited by examiner

*Primary Examiner* — David Sorkin
(74) *Attorney, Agent, or Firm* — Edwards Wildman Palmer LLP; George W. Neuner; Brian R. Landry

(57) ABSTRACT

The present invention is directed to mixers for viscometers and methods of using the same. Such inventions are applicable, for example, to industrial processes such as printing. One embodiment of the invention is directed to a viscosity control system including a viscosity sensor, a mixing element, a shaft fixedly attached to the mixing element, and an actuator interfacing with the viscosity sensor and the shaft. The annular mixing element is oscillatable about an axis lying in a plane tangent to a point on a wall of the mixing element. The shaft is centered about the axis. The actuator receives a signal from the viscosity sensor and rotates the shaft and the mixing element in an oscillating manner about the axis. In some embodiments, the shaft rotates through an angle of less than 360 degrees.

18 Claims, 2 Drawing Sheets

MIXERS FOR A VISCOMETER AND METHODS FOR USING THE SAME

RELATED APPLICATIONS

This application is a continuation under 35 U.S.C. §120 of International Application No. PCT/US2010/028467, filed Mar. 24, 2010, which claims priority to U.S. Provisional Patent Application Ser. No. 61/162,802, filed Mar. 24, 2009. The entire contents of each of these applications are hereby incorporated by reference herein.

FIELD OF INVENTION

The present invention is directed to mixers for viscometers and methods of using the same. Such inventions are applicable, for example, to industrial processes such as printing.

BACKGROUND

Viscosity control is essential in many of today's manufacturing and printing processes. Viscosity is the measure of the resistance of a fluid to deformation by either shear stress or extensional stress, but is commonly perceived as the "thickness" or resistance to flow of a fluid. Viscosity can be an important quality of a finished product (e.g. a lubricant, paint, or ink) or can affect a finished product (e.g. printed material). Perhaps more importantly, an inappropriate viscosity can adversely affect modern industrial equipment. For example, if the viscosity of printing ink falls outside of an acceptable viscosity ranges, not only is print quality affected, but the printing press can also become fouled.

In many processes, viscosity is continuously monitored and adjusted as needed. In many cases, viscosity is adjusted by adding additional solvent and/or solute to a mixture. Such additions will not immediately integrate the mixture, and therefore neither effect the desired viscosity adjustment nor allow the user to determine with a viscometer whether the adjustment was sufficient to produce the desired viscosity.

A variety of mixers are used to mix industrial chemical, such as printing ink. These mixers suffer from a variety of drawbacks. First, conventional mixers can cost approximately $500. This cost must be multiplied by the number of vats to be mixed. Second, many conventional mixers incorporate a significant amount of air into the mixture, especially where the fluid level in the vessel is low. In addition to distorting a viscosity measurement, this air can degrade processes such a printing.

Accordingly, there is a need for an affordable device capable of mixing liquid without incorporating air.

SUMMARY OF THE INVENTION

The present invention relates to a mixer for incorporation with a viscometer. One aspect of the invention provides a viscosity control system including: a viscosity sensor, a mixing element comprising a peripheral wall, a shaft fixedly attached to the mixing element, and an actuator interfacing with the viscosity sensor and the shaft. The mixing element is oscillatable about an axis lying in a plane tangent to a point on the wall of the mixing element. The shaft is centered about the axis. The actuator oscillates the shaft and the mixing element about the axis.

This aspect can have a variety of embodiments. The annular mixing element can include a plurality of apertures extending through the wall. The apertures can be substantially circular. The actuator can include a piston housed at least partially within a cylinder. The shaft can include includes a lever arm rigidly attached to the shaft. The piston can include a piston rod that extends at least partially outside of the cylinder to engage the lever arm and oscillate the shaft in a first direction when a pressure is applied to the piston. The system can include an air fitting through which compressed air is supplied to the cylinder to apply pressure to the piston within the cylinder.

The actuator can include a flexible element having a first end and a second end. The first end can be attached to the lever arm and the second end can be attached to the cylinder. The flexible element can move from a neutral position to an extended position when pressure is applied to the piston in the cylinder. The flexible element returns to the neutral position and rotates the shaft in a second direction when the pressure in the cylinder is released. The flexible element can be a coil spring. The mixing element can be a cylinder. The range of oscillation can be less than 360°.

Another aspect of the invention provides a fluid mixer including a mixing element comprising a peripheral wall; a shaft fixedly attached to the mixing element; and an actuator interfacing with the viscosity sensor and the shaft. The mixing element is oscillatable about an axis lying in a plane tangent to a point on the wall of the mixing element. The shaft is centered about the axis. The actuator oscillates the shaft and the mixing element about the axis.

Another aspect of the invention provides a method for controlling a viscosity of a fluid. The method includes measuring the viscosity of the fluid using a viscometer; positioning a mixing element within the fluid, the mixing element being oscillatable about an axis lying in a plane tangent to a point on a wall of the mixing element; adding a substance to the fluid in response to a signal sent by the viscometer; and oscillating the mixing element about the axis to mix the substance with the fluid.

This aspect can have a variety of embodiments. The annular mixing element can oscillate through an angle of less than 360 degrees. The oscillating motion of the mixing element can be accomplished using a reciprocating motion of a piston within a cylinder to move a shaft fixedly attached to the mixing element. The method can include using compressed air to move the piston within the cylinder. The method can be a computer-implemented method.

Another aspect of the invention provides a computer-readable medium whose contents cause a computer to perform a method for controlling a viscosity of a fluid. The method includes: measuring the viscosity of the fluid using a viscometer; positioning a mixing element within the fluid; adding a substance to the fluid in response to a signal sent by the viscometer; and oscillating the mixing element about the axis to mix the substance with the fluid. The mixing element is oscillatable about an axis lying in a plane tangent to a point on a wall of the mixing element.

This aspect can have a variety of embodiments. For example, the computer-readable medium can be non-transitory and tangible.

FIGURES

For a fuller understanding of the nature and desired objects of the present invention, reference is made to the following detailed description taken in conjunction with the accompanying drawing figures wherein like reference characters denote corresponding parts throughout the several views and wherein.

DESCRIPTION OF THE INVENTION

Figure 1:
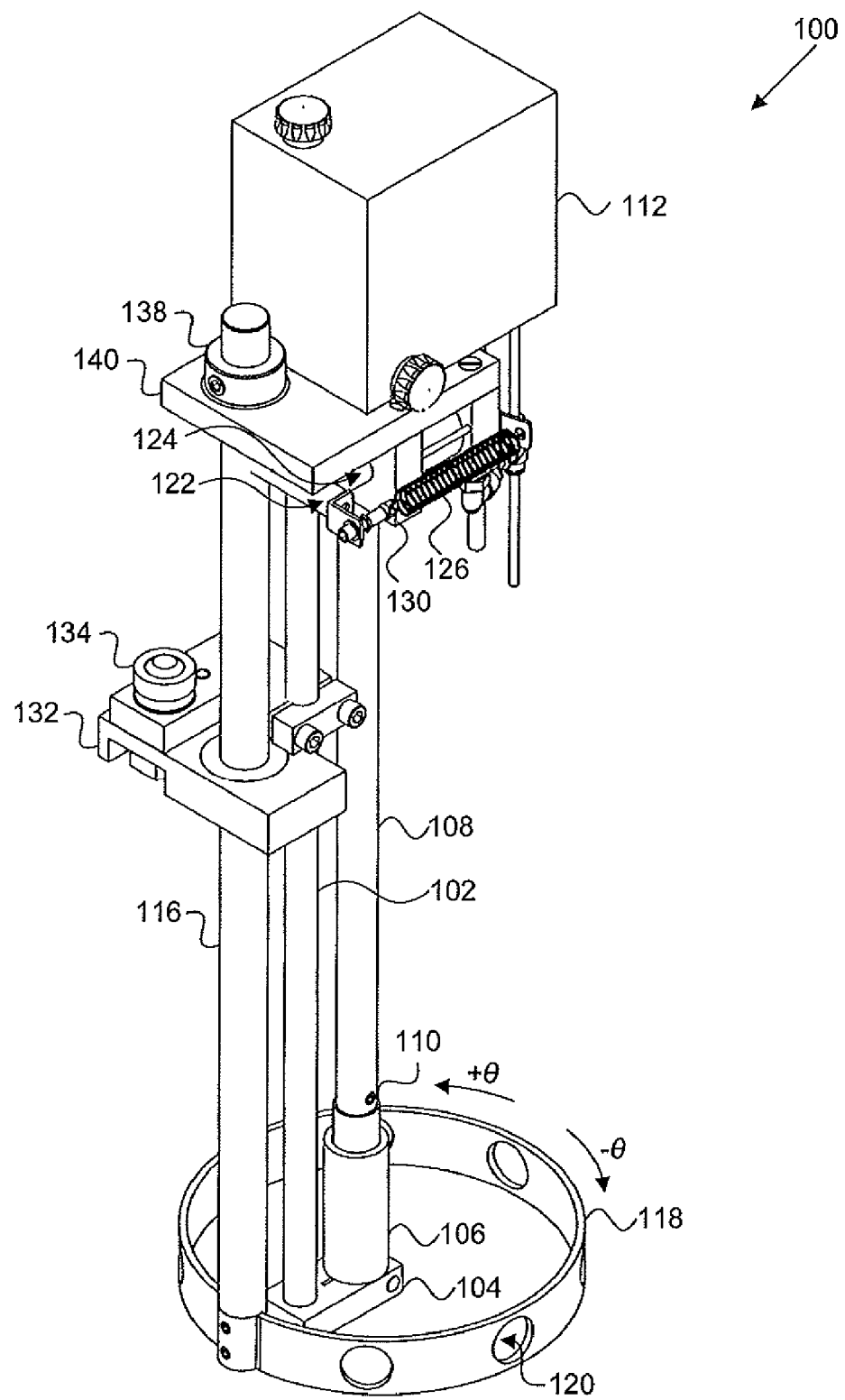
FIG. 1 is a perspective view of a system including a mixer and a viscometer according to one embodiment of the invention.

The present invention relates to a mixer for incorporation with a viscometer. Referring to FIG. 1, a viscosity control system 100 is provided. Viscosity control system 100 includes a viscometer. The viscometer can be any of a variety of known viscometers including falling piston, falling sphere, vibrational viscometers, rotation viscometers, Stabinger viscometers, and Stormer viscometers. Viscometers are available from a variety of sources including, for example, Norcross Corporation of Newton, Mass.

The embodiment depicted in FIG. 1 includes a failing piston viscometer. The falling piston viscometer includes a supporting shaft 102 connected to bracket 104 for supporting tube 106. Lifter cylinder 108 periodically lifted, thereby lifting piston 110. After piston 110 is raised so that tube 106 fills with the liquid to be measured, lifter cylinder 108 and piston 110 are released, allowing piston 110 to fall by force of gravity and displace fluid in tube 106. The piston 110, moving in close proximity to tube 106 approximates the parallel plates test for viscosity. Various embodiments of falling piston viscometers are described in U.S. Pat. Nos. 5,959,196; 4,154,094; 3,686,931; 3,677,070; and 3,304,765, the contents of which are hereby incorporated herein by reference. Although lifter cylinder 108 and piston 110 are described with separate labels in this description, in certain embodiments lifter cylinder 108 and piston 110 are a single component and can be fabricated from the same material.

In one embodiment, lifter cylinder 108 is actuated by a pneumatic actuator (not shown) contained within unit 112. Other means of actuation include electrical, mechanical, hydraulic, and the like.

Figure 2A:
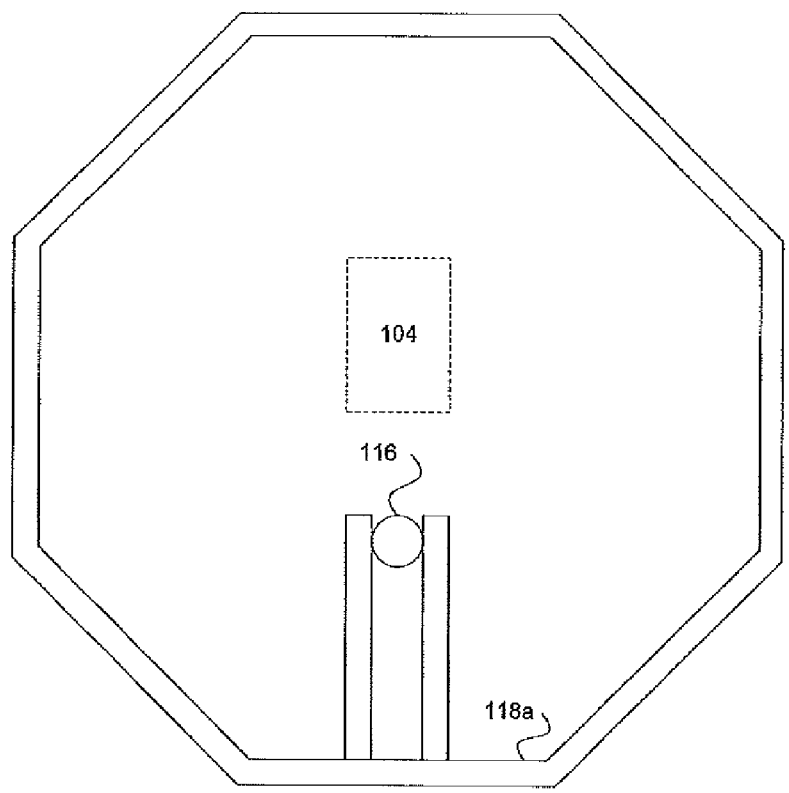
FIGS. 2A and 2B are top views of mixing elements according to embodiments of the invention.
Figure 2B:
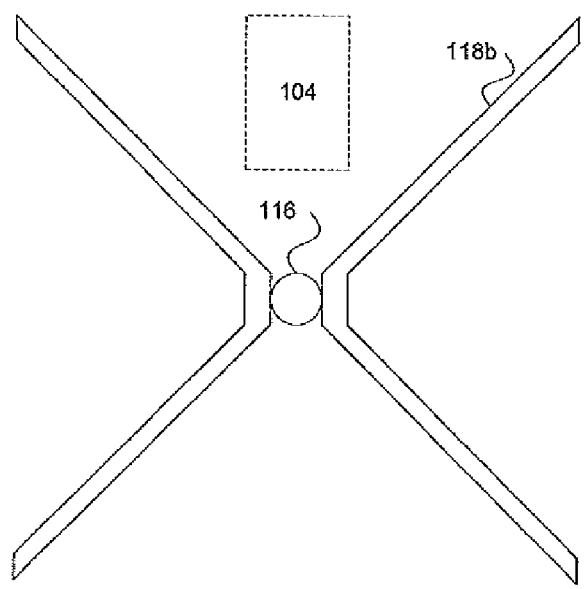

The mixer includes a mixing shaft 116 coupled with a mixing element 118. In some embodiments, the mixing element is a cylinder (i.e. a surface consisting of each of the straight lines that are parallel to a given straight line and pass through a given curve). In certain embodiments, mixing element is annular. In still other embodiments, mixing element 118 has a horizontal cross-section approximating a shape selected from the group consisting of: a square, a rectangle, a triangle, a circle, an oval, a polygon, a parallelogram, a rhombus, an annulus, a crescent, a semicircle, an ellipse, a super ellipse, and a deltoid. An exemplary mixing element 118a is depicted in FIG. 2A. In still other elements, such as those depicted in FIG. 2B, mixing element 118b is not continuous, but rather comprises at least one open end. Such embodiments include elements having a horizontal cross-section approximating a 'Y', a 'U', an 'X', and the like.

In some embodiments, mixing element 118 has a solid peripheral wall. In other embodiments, mixing element 118 includes one or more apertures 120 in the wall that promote mixing of the liquid as mixing element is moved. Apertures 120 can be circular or have a cross-section, e.g., approximating a shape selected from the group consisting of: a square, a rectangle, a triangle, a circle, an oval, a polygon, a parallelogram, a rhombus, an annulus, a crescent, a semicircle, an ellipse, a super ellipse, and a deltoid.

Mixing shaft 116 and mixing element 118 are attached by a fastening means such as a nails, screws, bolts, pins, rivets, welding, brazing, soldering, adhesives, crimping, press fitting, and the like. Mixing element 118 can be removably attached so that various mixing elements can be used with the same mixer to reflect various vessel shapes and fluid characteristics.

Mixing shaft 116 can be oscillated by a number of devices. In the embodiment of the invention illustrated by FIG. 1, mixing shaft is coupled with a lever arm 122. Lever arm 122 contacts piston 124, which is in one embodiment, pneumatically actuated. As lifter cylinder 108 is raised, air flows to cylinder 130, causing piston 124 to extend outwards, pushing lever arm 122, and rotating mixing shaft 116 and mixing element 118 in the negative $\theta$ direction. When air flow ceases, extension spring 126 acts depresses piston 124 and rotating mixing shaft 116 and mixing element 118 in the positive $\theta$ direction.

In embodiments of the invention wherein the mixing element 118 is configured at the same height as one or more of viscometer elements 102, 104, 106, 108, or 110, the range of oscillation of mixing element 118 will generally be limited to a range less than 360°. For example, the range of oscillation can be about 270°, 180°, 90°, 60°, 45°, 30°, and the like. In embodiments of the invention wherein the mixing element is configured at a height below viscometer elements 102, 104, 106, 108, or 110, the range of oscillation of mixing element 118 can extend beyond 360°.

A number of devices can be used to return piston to its resting position. For example, a cylinder 130 can contain a compression coil spring to push piston 124 back to a resting position. Cylinder 130 can include a bleed valve to allow for air to escape from cylinder 130 when air flow into the cylinder 130 ceases. Alternatively, air may return through a tube that provides the air. In another embodiment, mixer shaft 116 is coupled with a spring to return mixer shaft 116 and piston 124 to a starting position. In another embodiment, a tension spring is coupled to supporting shaft 102 and lever 122.

In other embodiments, piston 124 and/or mixing shaft 116 are operated by electrical, mechanical, or hydraulic means such as a motor or a servo.

Lever 122 and piston 124 can be coupled in a variety of configurations. In one embodiment, lever 122 and piston 124 are held together, in whole or in part, by pressure by compression and/or tension. Such a configuration can be obtained through the embodiments described above wherein a spring applies force to push lever 122 against piston 124.

In another embodiment, lever and piston are coupled by a mechanical linkage or linkages. Such linkages include nails, screws, bolts, pins, rivets, hinges, chains, cables, rope, string, and the like.

In some embodiments, bracket 132 provides support for mixer shaft 116 and supporting shaft 102. Bracket 132 can include a variety of fasteners 134 and holes for coupling bracket 132 with a vessel holding a liquid.

In still further embodiments, collar 138 couples with mixer shaft 116 to support mixer shaft 116 in bracket 140. Collar 138 can be adjustable (for example, by loosening a screw) in order to allow for the height of mixing element with regard to tube 106 to be adjusted. In other embodiments, mixing shaft 116 is machined to comprise a top portion having a larger diameter than the bottom portion. Such an embodiment would support the mixing shaft without a collar 138.

The components described herein can be fabricated from a variety of materials including, but not limited to, copper, steel (including unfinished or galvanized), cast iron, brass, aluminum, titanium, nickel, other metals and metal alloys, polyvinyl chloride (PVC), chlorinated polyvinyl chloride (CPVC), cross-linked high-density polyethylene (PEX), polybutylene (PB), acrylonitrile butadiene styrene (ABS), and the like. Such materials should be substantially inert to the fluid to be mixed. Materials can be formed into the components described herein by a variety of processes including casting, molding, machining, milling, stamping, and the like.

The apparatus described herein allows for the mixing of low levels of fluids without introducing air to the fluid. As depicted in FIG. 1, mixing element 118 can, in some embodiments, have a height shorter than the height of tube 106. Accordingly, if there is sufficient ink in the vessel to allow for the measurement of viscosity, mixing element will be submerged.

Although the embodiments described herein discuss the mixer integrated with a viscometer, the invention encompasses mixers that are capable of operation with or without a viscometer. Such mixers can be configured for mounting on a viscometer and/or according to the same or similar principles described herein.

The mixer provided herein can configured to operate in a variety of ways. In one embodiment, the mixer (and viscometer, if combined) are introduced to a vessel, which in some embodiments will or will not contain fluid at the time of mixer introduction. The mixer can be configured to operating independently from the viscometer or dependent on the viscometer.

In an independent configuration, the movement of mixing element 118 is not affected by the operation of the viscometer. For example, mixer continues to oscillate regardless of whether the viscometer is sampling the fluid.

In a dependent configuration, the movement of mixing element 118 is affected by the operation of the viscometer. For example, the mixer can normally operate at a set oscillation speed and/or frequency, but cease or reduce the oscillation speed/frequency when the viscometer is sampling the fluid. The viscometer can return to the normal oscillation speed frequency when the sampling is completed.

The foregoing specification and the drawings forming part hereof are illustrative in nature and demonstrate certain preferred embodiments of the invention. It should be recognized and understood, however, that the description is not to be construed as limiting of the invention because many changes, modifications and variations may be made therein by those of skill in the art without departing from the essential scope, spirit or intention of the invention.

The invention claimed is:

1. A viscosity control system comprising:
   a viscosity sensor;
   a mixing element comprising a peripheral wall, the mixing element oscillatable about an axis lying in a plane tangent to a point on the wall of the mixing element;
   a shaft fixedly attached to the mixing element, the shaft being centered about the axis; and
   an actuator interfacing with the viscosity sensor and the shaft, wherein the actuator oscillates the shaft and the mixing element about the axis.

2. The viscosity control system of claim 1, wherein the mixing element includes a plurality of apertures extending through the wall.

3. The viscosity control system of claim 2, wherein the apertures are substantially circular.

4. The viscosity control system of claim 1, wherein the actuator comprises a piston housed at least partially within a cylinder.

5. The viscosity control system of claim 4, wherein the shaft includes a lever arm rigidly attached to the shaft and the piston includes a piston rod that extends at least partially outside of the cylinder to engage the lever arm and oscillate the shaft in a first direction when a pressure is applied to the piston.

6. The viscosity control system of claim 5, further comprising an air fitting through which compressed air is supplied to the cylinder to apply pressure to the piston within the cylinder.

7. The viscosity control system of claim 5, wherein the actuator further comprises a flexible element having a first end and a second end, the first end being attached to the lever arm and the second end being attached to the cylinder, the flexible element moving from a neutral position to an extended position when the pressure is applied to the piston in the cylinder, the flexible element returning to the neutral position and rotating the shaft in a second direction when the pressure in the cylinder is released.

8. The viscosity control system of claim 7, wherein the flexible element is a coil spring.

9. The viscosity control system of claim 1, wherein the mixing element is a cylinder.

10. The viscosity control system of claim 1, wherein the range of oscillation is less than 360°.

11. The fluid mixer of claim 1, wherein the viscosity sensor communicates with the actuator to cease or reduce oscillation speed or frequency of the mixing element when the viscosity sensor is sampling a fluid.

12. A fluid mixer comprising:
    a mixing element comprising a peripheral wall, the mixing element oscillatable about an axis lying in a plane tangent to a point on the peripheral wall of the mixing element;
    a shaft fixedly attached to the mixing element, the shaft being centered about the axis; and
    an actuator interfacing with the shaft, wherein the actuator oscillates the shaft and the mixing element about the axis.

13. A method for controlling a viscosity of a fluid, the method comprising:
    providing a viscosity control system including:
    a viscosity sensor;
    a mixing element comprising a peripheral wall, the mixing element oscillatable about an axis lying in a plane tangent to a point on the wall of the mixing element;
    a shaft fixedly attached to the mixing element, the shaft being centered about the axis; and
    an actuator interfacing with the viscosity sensor and the shaft, wherein the actuator oscillates the shaft and the mixing element about the axis;
    measuring the viscosity of the fluid using the viscosity sensor;
    positioning the mixing element within the fluid;
    adding a substance to the fluid in response to a signal sent by the viscosity sensor; and
    oscillating the mixing element about the axis to mix the substance with the fluid.

14. The method of claim 13, wherein the annular mixing element is oscillates through an angle of less than 360 degrees.

15. The method of claim 13, wherein the oscillating motion of the mixing element is accomplished using a reciprocating motion of a piston within a cylinder to move a shaft fixedly attached to the mixing element.

16. The method of claim 14, further comprising using compressed air to move the piston within the cylinder.

17. The method of claim 13, wherein the method is computer-implemented method.

18. The method of claim 13, further comprising ceasing or reducing oscillation speed or frequency of the mixing element when the viscosity sensor is sampling the fluid.

* * * * *